United States Patent [19]
Plath et al.

[11] Patent Number: 5,744,425
[45] Date of Patent: Apr. 28, 1998

[54] SACCHARIN DERIVATIVES

[75] Inventors: Peter Plath, Frankenthal; Uwe Kardorff, Mannheim; Wolfgang von Deyn, Neustadt; Stefan Engel, Wörrstadt; Jürgen Kast, Böhl-Iggelheim; Harald Rang, Altrip; Hartmann König, Heidelberg; Matthias Gerber, Limburgerhof; Helmut Walter, Obrigheim; Karl-Otto Westphalen, Speyer, all of Germany

[73] Assignee: BASF Aktiengesellschaft, Ludwigshafen, Germany

[21] Appl. No.: 776,582

[22] PCT Filed: Jul. 27, 1995

[86] PCT No.: PCT/EP95/02973

§ 371 Date: Feb. 3, 1997

§ 102(e) Date: Feb. 3, 1997

[87] PCT Pub. No.: WO96/05182

PCT Pub. Date: Feb. 22, 1996

[30] Foreign Application Priority Data

Aug. 8, 1994 [DE] Germany .................. 44 27 995.7

[51] Int. Cl.⁶ .................. C07D 275/06; A01N 43/80
[52] U.S. Cl. .................. 504/269; 548/210
[58] Field of Search .................. 548/210; 504/269

[56] References Cited

U.S. PATENT DOCUMENTS

| | | | |
|---|---|---|---|
| 4,249,937 | 2/1981 | Iwataki et al. | 71/97 |
| 4,410,353 | 10/1983 | Theissen | 71/91 |
| 4,422,864 | 12/1983 | Becker et al. | 71/88 |
| 4,447,634 | 5/1984 | Lee | 560/13 |
| 4,654,073 | 3/1987 | Jahn et al. | 71/88 |
| 4,780,127 | 10/1988 | Michaely et al. | 71/103 |
| 4,851,032 | 7/1989 | Jahn et al. | 71/94 |
| 4,909,835 | 3/1990 | Tobler | 71/103 |
| 4,956,003 | 9/1990 | Jahn et al. | 71/92 |
| 5,026,899 | 6/1991 | Tobler | 560/122 |
| 5,055,125 | 10/1991 | Matolcsy et al. | 71/88 |
| 5,110,343 | 5/1992 | Ueda et al. | 71/88 |
| 5,132,462 | 7/1992 | Tobler | 568/31 |
| 5,169,988 | 12/1992 | Tobler | 568/31 |
| 5,270,340 | 12/1993 | Kunisch et al. | 514/538 |
| 5,468,905 | 11/1995 | Suzuki et al. | 568/346 |

FOREIGN PATENT DOCUMENTS

| | | |
|---|---|---|
| 2141763 | 8/1995 | Canada . |
| 71 707 | 2/1983 | European Pat. Off. . |
| 142 741 | 5/1985 | European Pat. Off. . |
| 186 118 | 7/1986 | European Pat. Off. . |
| 243 313 | 10/1987 | European Pat. Off. . |
| 319075 | 6/1989 | European Pat. Off. . |
| 376072 | 7/1990 | European Pat. Off. . |
| 594 257 | 4/1994 | European Pat. Off. . |
| 36 07 343 | 9/1986 | Germany . |
| 44 03 670 | 9/1995 | Germany . |
| 44 27 996 | 2/1996 | Germany . |
| 92/13821 | 8/1992 | WIPO . |

OTHER PUBLICATIONS

Justus Liebig', Annalen der Chemie, Wallach et al., Band 427, 1922.

Berichte der Deutschen Chemischen Gesellschaft, Berlin, 1880.

Chem. Abst. BE 768381 (1971).

Chem. Abst. JA 7335457 (1973).

Berichte der Deutschen Chemischen Gesellschaft Berlin, 1892.

*Primary Examiner*—Johann Richter
*Assistant Examiner*—Laura Crosslutz
*Attorney, Agent, or Firm*—Keil & Weinkauf

[57] ABSTRACT

Saccharin derivatives of the formula I

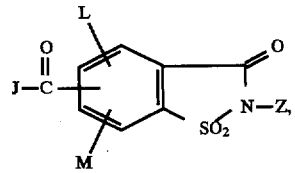

where the substituents have the following meanings:

L and M are hydrogen, alkyl, alkoxy, alkylthio, chlorine, cyano, methylsulfonyl, nitro or trifluoromethyl;

Z is hydrogen, alkyl, cycloalkyl, alkenyl, alkynyl, acyl, or benzyl or phenyl which are unsubstituted or substituted by halogen or alkyl;

J is a 2-linked, unsubstituted or substituted cyclohexane-1,3-dione ring, are described.

7 Claims, No Drawings

SACCHARIN DERIVATIVES

This application is 371 of PCT/EP95/02973 filed Jul. 27, 1995.

The present application relates to saccharin derivatives of the formula I

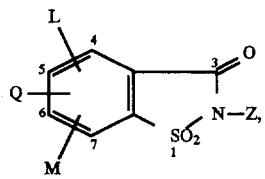

where the substituents have the following meanings:
L and M are hydrogen, $C_1$–$C_4$-alkyl, $C_1$–$C_4$-alkoxy, $C_1$–$C_4$-alkylthio, chlorine, cyano, methylsulfonyl, nitro or trifluoromethyl;
Z is hydrogen, $C_1$–$C_4$-alkyl, $C_3$–$C_8$-cycloalkyl, $C_3$–$C_6$-alkenyl, $C_3$–$C_5$-alkynyl, $C_1$–$C_4$-acyl, benzyl or phenyl, the phenyl rings in each case being unsubstituted or substituted by halogen or $C_1$–$C_4$-alkyl;
Q is a radical CO—J;
J is a 2-linked cyclohexane-1,3-dione ring of the formula II

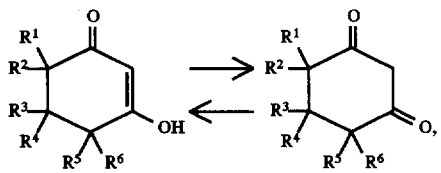

where either $R^1$ to $R^6$ are hydrogen or methyl, or, if $R^1$, $R^2$, $R^3$, $R^5$ and $R^6$ are hydrogen, $R^4$ is 2-ethylthiopropyl, tetrahydropyran-3-yl, tetrahydropyran-4-yl, tetrahydrothiopyran-3-yl or 1-methylthiocyclopropyl, or, if $R^1$, $R^4$ and $R^5$ are hydrogen and $R^6$ is methyl, $R^2$ and $R^3$ form a three-membered ring such that a 2-linked bicyclo[4.1.0]heptane ring of the formula III results

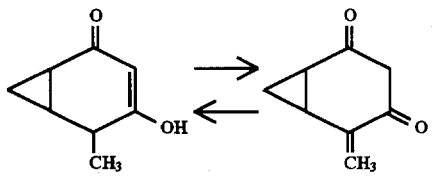

and agriculturally customary salts of the compounds I.

The invention further relates to herbicidal compositions containing the compounds I, and methods of controlling undesired plant growth using the saccharin derivatives I. Moreover, the present invention also encompasses intermediates for preparing the final products I according to the invention and preparation processes for the products I, starting from the novel intermediates of the formulae IV and V

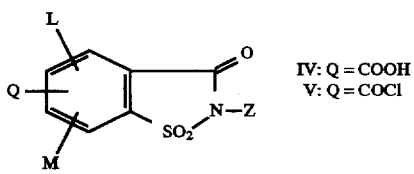

IV: Q = COOH
V: Q = COCl where the remaining radicals L, M and Z have the abovementioned meanings.

Saccharin derivatives having herbicidal action cannot be inferred from the prior art. However, unsubstituted saccharin (o-sulfo-benzimide, i.e. L, M, Q and Z in formula I=H) has been known as a synthetic sweetener for a long time. 4-Hydroxysaccharin is further known as a sweetener (German Offenlegungsschrift 3 607 343). The use of saccharin derivatives in pest control is also known, e.g. JP publication 72/00419, 73/35457 (fungicides) and in pharmacy, e.g. EP-A 594 257 and literature references mentioned therein.

Herbicidally active 2-aroylcyclohexanediones are a subject of the earlier German Application P 44 03 670. Among other things, linkage with saccharin and N-alkylsaccharin is mentioned without giving a preparation route for these compounds.

Heterocyclic compounds having a sulfonamide-containing ring have been disclosed as herbicides, a typical representative which can be mentioned here being bentazone

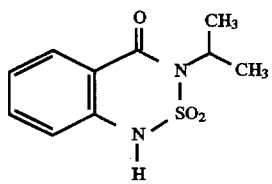

It is an object of the present invention to make available novel herbicides having a basic structure which was hitherto unknown for this indication.

We have found that this object is achieved by the compounds I and the intermediates IV and V defined at the outset. The intermediates IV and their preparation are the subject of the parallel German Application DE-A 44 27 996.

Compounds of the formula I are obtained by acylating compounds of the formula II or III with an acid chloride of the formula V and rearranging to give saccharin derivatives of the formula I.1:

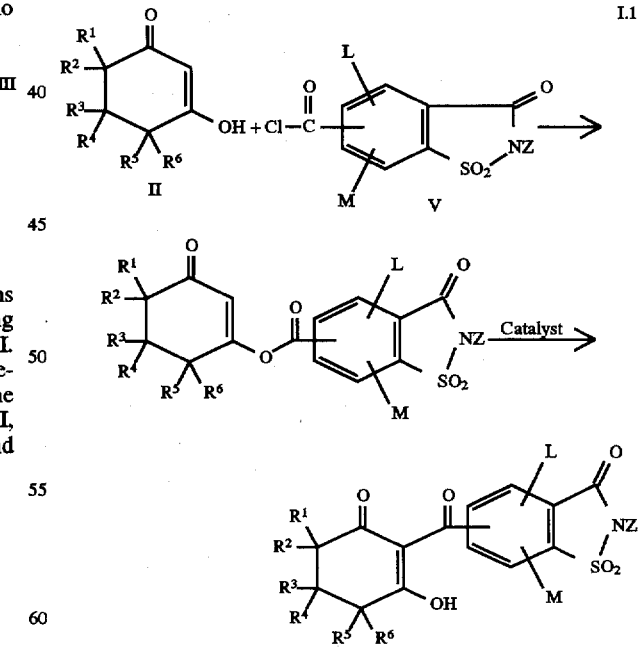

In the abovementioned formulae, L and M have the meaning given at the outset and Z is hydrogen, $C_1$–$C_4$-alkyl, $C_3$–$C_8$-cycloalkyl, $C_3$–$C_6$-alkenyl, $C_3$–$C_5$-alkynyl, $C_1$–$C_4$-acyl or benzyl or phenyl which is unsubstituted or substituted by halogen or $C_1$–$C_4$-alkyl.

The first step of the reaction sequence, the acylation, is carried out in a generally known manner, e.g. by addition of an acid chloride of the formula V to the solution or suspension of a cyclohexane-1,3-dione II or III in the presence of an auxiliary base. The reactants and the auxiliary base are in this case expediently employed in equimolar amounts. A small excess, e.g. from 1.2 to 1.5 mol equivalents, based on II or III, of the auxiliary base can be advantageous in certain circumstances.

Suitable auxiliary bases are tertiary alkylamines, pyridine or alkali metal carbonates. The solvents used can be e.g. methylene chloride, diethyl ether, toluene or ethyl acetate.

During the addition of the acid chloride, the reaction mixture is preferably cooled to from 0° to 10° C., then stirred at from 20° to 100° C., in particular from 25° to 50° C., until the reaction is complete. Working up is carried out in a customary manner, e.g. the reaction mixture is poured into water and the useful product is extracted, e.g. with methylene chloride. After drying the organic phase and removing the solvent, the crude enol ester can be employed for the rearrangement without further purification. Preparation examples for benzoyl enol esters of cyclohexane-1,3-diones are found e.g. in EP-A 186 118 or U.S. Pat. No. 4,780,127.

The rearrangement of the enol esters to the compounds of the formula I.1 is expediently carried out at from 20° C. to 40° C. in a solvent and in the presence of an auxiliary base, and with the aid of a cyano compound as a catalyst.

The solvents used can be e.g. acetonitrile, methylene chloride, 1,2-dichloroethane, ethyl acetate or toluene. The preferred solvent is acetonitrile. Suitable auxiliary bases are tertiary alkylamines, pyridine or alkali metal carbonates, which are preferably employed in equimolar amount or an up to four-fold excess, based on the benzoyl enol ester. A preferred auxiliary base is triethylamine in a doubled amount.

A suitable catalyst is e.g. potassium cyanide or acetone cyanohydrin, preferably in an amount of from 1 to 50 mol %, based on the enol ester. Acetone cyanohydrin is preferably added, e.g. in an amount of from 5 to 15, in particular 10, mol %. Examples of the cyanide-catalyzed rearrangement of enol esters of cyclohexane-1,3-diones are found e.g. in EP-A 186 118 or U.S. Pat. No. 4,780,127.

Working up is carried out in a manner known per se, e.g. the reaction mixture is acidified with dilute mineral acids such as 5% strength hydrochloric acid or sulfuric acid and extracted with an organic solvent such as methylene chloride or ethyl acetate. For purification, the extract is extracted with cold 5 to 10% strength alkali metal carbonate solution, the final product passing into the aqueous phase. The product of the formula I is precipitated by acidifying the aqueous solution or extracted again with methylene chloride, dried and then freed from the solvent.

The 1,3-diketones of the formulae II and III used as a starting material are known and can be prepared by processes known per se (cf. EP-A 71 707, EP-A 142 741, EP-A 243 313, U.S. Pat. No. 4 249 937 and WO 92/13821). Cyclohexane-1,3-dione and dimedone are commercially available compounds.

The starting substances of the formula V are prepared in a manner known per se by reaction of the saccharincarboxylic acid derivatives IV with thionyl chloride.

Saccharincarboxylic acids IV are known in some cases (4-COOH: Zincke, Liebigs Ann. 427 (1922) 231, 5-COOH: Jacobsen, Chem. Ber. 13 (1880), 1554, 6-COOH: Weber, Chem. Ber. 25 (1892), 1740). Further, the preparation of 4-chlorosaccharin-5-carboxylic acid is described in German offenlegungsschrift 36 07 343.

Saccharincarboxylic acids IV can also be obtained by reacting corresponding bromo- or iodo-substituted saccharin derivatives of the formula A1

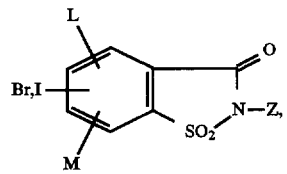

where L, M and Z have the abovementioned meanings, or if Z≠H compounds of the formula A2

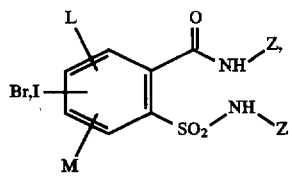

with carbon monoxide and water at elevated pressure in the presence of a palladium, nickel, cobalt or rhodium transition metal catalyst and a base.

If, for example, L is methyl and M and Z are hydrogen, the reaction sequence can be shown as follows:

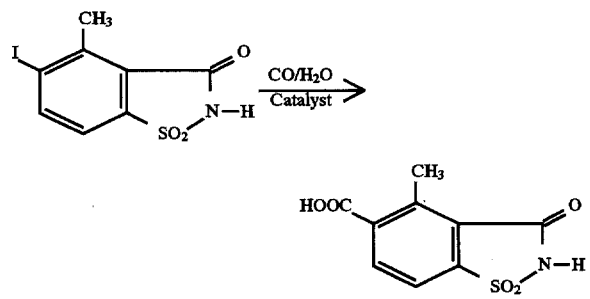

The catalysts nickel, cobalt, rhodium and in particular palladium can be present in metallic form or in the form of customary salts, such as in the form of halogen compounds, e.g. $PdCl_2$, $RhCl_3 \cdot H_2O$, acetates, e.g. $Pd(OAc)_2$, cyanides etc. in the known valency states. Metal complexes with tertiary phosphines, metal alkylcarbonyls, metal carbonyls, e.g. $CO_2(CO)_8$, $Ni(CO)_4$, metal carbonyl complexes with tertiary phosphines, e.g. $(PPh_3)_2Ni(CO)_2$, or transition metal salts complexed with tertiary phosphines can further be present. The last-mentioned embodiment is particularly preferred in the case of palladium as a catalyst. The nature of the phosphine ligands here is widely variable. For example, they can be represented by the following formulae:

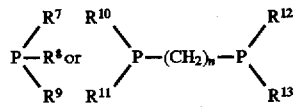

where n is the numbers 1, 2, 3 or 4 and the radicals $R^7$ to $R^{13}$ are low-molecular weight alkyl, e.g. $C_1$–$C_6$-alkyl, aryl or $C_1$–$C_4$-alkyl-aryl, e.g. benzyl, phenethyl or aryloxy. Aryl is, e.g. naphthyl, anthryl and preferably unsubstituted or substituted phenyl, it only being necessary with respect to the substituents to take into account their inertness to the carboxylation reaction, otherwise they can be widely varied and include all inert C-organic radicals such as $C_1$–$C_6$-alkyl radicals, e.g. methyl, carboxyl radicals such as COOH, COOM (M is e.g. an alkali metal, alkaline earth metal or ammonium salt), or C-organic radicals bonded via oxygen, such as $C_1$–$C_6$-alkoxy radicals.

The preparation of the phosphine complexes can be carried out in a manner known per se, e.g. as described in the documents mentioned at the outset. For example, commercially available metal salts such as $PdCl_2$ or $Pd(OCOCH_3)_2$ are used as starting materials and the phosphine, e.g. $P(C_6H_5)_3$, $P(n-C_4H_9)_3$, $PCH_3(C_6H_5)_2$ or 1,2-bis (diphenylphosphino)ethane added.

The amount of phosphine, based on the transition metal, is customarily from 0 to 20, in particular from 0.1 to 10, mol equivalents, particularly preferably from 1 to 5 mol equivalents.

The amount of transition metal is not critical. For cost reasons, of course, rather a small amount, e.g. from 0.1 to 10 mol %, in particular from 1 to 5 mol %, based on the starting substance A1 or A2, will be used.

Reaction with carbon monoxide and at least equimolar amounts of water, based on the starting substances A1 or A2, is carried out to prepare the saccharincarboxylic acids IV. The reaction component water can simultaneously also be used as a solvent, i.e. the maximum amount is not critical.

However, it can also be advantageous, depending on the nature of the starting substances and the catalysts used, to use another inert solvent or the base used for the carboxylation as a solvent instead of the reaction component.

Suitable inert solvents for carboxylation reactions are customary solvents such as hydrocarbons, e.g. toluene, xylene, hexane, pentane, cyclohexane, ethers, e.g. methyl tert-butyl ether, tetra-hydrofuran, dioxane, dimethoxyethane, substituted amides such as dimethylformamide, persubstituted ureas such as tetra-$C_1$–$C_4$-alkyl-ureas, or nitrites such as benzonitrile or acetonitrile.

In a preferred embodiment of the process, one of the reaction components, in particular the base, is used in an excess such that no additional solvent is necessary.

Bases suitable for the process are all inert bases which are able to bind the hydrogen iodide or hydrogen bromide liberated in the reaction. Examples which can be mentioned here are tertiary amines such as tert-alkylamines, e.g. trialkylamines such as tri-ethylamine, cyclic amines such as N-methylpiperidine or N,N'-di-methylpiperazine, pyridine, alkali metal carbonates or hydrogen carbonates, or tetraalkyl-substituted urea derivatives such as tetra-$C_1$–$C_4$-alkylurea, e.g. tetramethylurea.

The amount of base is not critical, 1 to 10, in particular 1 to 5, mol customarily being used. When the base is simultaneously used as a solvent, as a rule the amount is proportioned such that the reaction components are dissolved, unnecessarily high excesses being avoided for reasons of practicability in order to save costs, to be able to employ small reaction vessels and to guarantee maximum contact of the reaction components.

During the reaction, the carbon monoxide pressure is adjusted such that an excess of CO, based on A1 or A2, is always present. Preferably, the carbon monoxide pressure at room temperature is from 1 to 250 bar, in particular from 5 to 150 bar, of CO.

As a rule, the carbonylation is carried out batchwise or continuously at from 20° to 250° C., in particular at from 30° to 150° C. In the case of batchwise operation, carbon monoxide is expediently injected into the reaction mixture continuously to maintain a constant pressure.

The products are isolated from the resulting reaction mixture in a customary manner, e.g. by distillation.

The starting substances A1 and A2 required for the reaction are known or can be prepared in a manner known per se. They can be obtained either by permanganate oxidation of iodo-substituted 2-methylbenzenesulfonamides or by Sandmeyer reaction of aminosaccharides. Aminosaccharins are obtained according to known methods by reduction of nitrosaccharides which, in turn, are either known (Kastle, Amer. Chem. Journal 11 (1889), 184 or DRP 551423 (1930)) or are synthesized from suitable nitrobenzene derivatives (Liebigs Ann. 669 (1963), 85) or benzenesulfonamides in a manner known from the literature.

Moreover, they can be obtained analogously to the preparation procedures of Examples 1 to 12.

With respect to the intended use, saccharin derivatives of the formula I are preferred where the radicals L and M are hydrogen, methyl, methoxy, methylthio, chlorine, cyano, methylsulfonyl, nitro or trifluoromethyl. Saccharin derivatives I are furthermore preferred where one of the radicals L or M or both radicals L and M are not hydrogen.

In formula I, the radicals $R^1$ to $R^6$ are either all hydrogen or one, two or three radicals are methyl and the remaining radicals are hydrogen. In addition to the unsubstituted cycle ($R^1$ to $R^6$=H), the radical combination $R^3+R^4=CE_3$ and $R^1$, $R^2$, $R^5$ and $R^6$=H is particularly preferred.

The radical Z is particularly preferably one of the C-organic radicals mentioned, in particular methyl, ethyl, propargyl, acetyl or phenyl.

Particularly preferred active compounds can be taken from Tables 1 to 7.

The compounds I can be present in the form of their agriculturally utilizable salts, the nature of the salt in general not mattering. Customarily, the salts of those bases which do not adversely affect the herbicidal action of I are suitable.

Suitable basic salts are particularly those of the alkali metals, preferably the sodium and potassium salts, those of the alkaline earth metals, preferably calcium, magnesium and barium salts and those of the transition metals, preferably manganese, copper, zinc and iron salts as well as the ammonium salts, which can carry one to three $C_1$–$C_4$-alkyl or hydroxy-$C_1$–$C_4$-alkyl substituents and/or a phenyl or benzyl substituent, preferably diisopropylammonium, tetramethylammonium, tetrabutylammonium, trimethylbenzylammonium and trimethyl-(2-hydroxyethyl)ammonium salts, the phosphonium salts, the sulfonium salts, preferably tri($C_1$–$C_4$)-alkylsulfonium salts, and the sulfoxonium salts, preferably tri($C_1$–$C_4$)-alkylsulfoxonium salts.

The compounds I, the herbicidal compositions containing them and their environmentally tolerable salts of, for example, alkali metals, alkaline earth metals or ammonia and amines or the herbicidal compositions containing them can control broad-leaved weeds and grass weeds highly effectively in crops such as wheat, rice, maize, soybeans and cotton without noticeably damaging the crop plants. This effect occurs especially at low application rates.

Taking into account the versatility of the application methods, the compounds I or compositions containing them can also be employed in a further number of crop plants for the elimination of undesired plants. Examples of suitable crops are the following:

*Allium cepa, Ananas comosus, Arachis hypogaea, Asparagus officinalis, Beta vulgaris* spp. *altissima, Beta vulgaris* spp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max,*

*Gossypium hirsutum*, (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spp., Manihot esculenta, Medicago sativa, Musa spp., Nicotiana tabacum* (*N. rustica*), *Olea europaea, Oryza sativa, Phaseolus lunatus, Phaseolus vulgaris, Picea abies, Pinus spp., Pisum sativum, Prunus avium, Prunus persica, Pyrus communis, Ribes sylvestre, Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, Vicia faba, Vitis vinifera, Zea mays*.

Moreover, the compounds I can also be employed in crops which have been made largely resistant to the action of I or other herbicides by breeding and/or by means of genetic engineering methods.

The application of the herbicidal compositions or of the active compounds can be carried out preemergence of postemergence. If the active compounds are less tolerable for certain crop plants, application techniques can be used in which the herbicidal compositions are sprayed with the aid of the spray equipment such that the leaves of the sensitive crop plants are not affected if possible, while the active compounds reach the leaves of undesired plants growing under them or the uncovered soil surface (post-directed, lay-by).

The compounds I or the herbicidal compositions containing them can be applied by spraying, atomizing, dusting, scattering or watering in the form of directly sprayable aqueous solutions, powders, suspensions, even high-percentage aqueous, oily or other suspensions or dispersions, emulsions, oil dispersions, pastes, dusting compositions, scattering compositions or granules. The application forms depend on the intended uses; if possible they should in each case guarantee the finest dispersion of the active compounds according to the invention.

Suitable inert auxiliaries for the preparation of directly sprayable solutions, emulsions, pastes or oil dispersions are essentially: mineral oil fractions of medium to high boiling point such as kerosene or diesel oil, further coal tar oils and oils of vegetable or animal origin, aliphatic, cyclic and aromatic hydrocarbons, e.g. paraffins, tetrahydronaphthalene, alkylated naphthalene or their derivatives, alkylated benzenes and their derivatives, alcohols such as methanol, ethanol, propanol, butanol and cyclohexanol, ketones such as cyclohexanone or strongly polar solvents, e.g. amines such as N-methylpyrrolidone, or water.

Aqueous application forms can be prepared from emulsion concentrates, suspensions, pastes, wettable powders or water-dispersable granules by addition of water. To prepare emulsions, pastes or oil dispersions, the substances can be homogenized in water, as such or dissolved in an oil or solvent, by means of wetting agents, adhesives, dispersants or emulsifiers. However, concentrates consisting of active substance, wetting agent, adhesive, dispersant or emulsifier and possibly solvents or oil which are suitable for dilution with water can also be prepared.

Suitable surface-active substances are the alkali metal, alkaline earth metal or ammonium salts of aromatic sulfonic acids, e.g. lignosulfonic, phenolsulfonic, naphthalenesulfonic and dibutylnaphthalenesulfonic acid, as well as of fatty acids, alkyl- and alkylarylsulfonates, alkyl-, lauryl ether and fatty alcohol sulfates, and also salts of sulfated hexa-, hepta- and octa-decanols as well as of fatty alcohol glycol ethers, condensation products of sulfonated naphthalene and its derivatives with formaldehyde, condensation products of naphthalene or of the naphthalenesulfonic acids with phenol and formaldehyde, polyoxyethylene octyl phenol ethers, ethoxylated isooctyl-, octyl- or nonyl-phenol, alkylphenyl or tributylphenylpolyglycol ethers, alkylaryl polyether alcohols, isotridecyl alcohol, fatty alcoholethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powder, scattering and dusting compositions can be prepared by mixing or joint grinding of the active substances with a solid carrier.

Granules, e.g. coated, impregnated and homogeneous granules can be prepared by binding of the active compounds to solid carriers. Solid carriers are mineral earth such as silicic acids, silica gels, silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and vegetable products such as cereal flour, tree bark meal, wood meal and nutshell meal, cellulose powder or other solid carriers.

In general, the formulations contain from 0.01 to 95% by weight, preferably from 0.5 to 90% by weight, of active compound. The active compounds are employed here in a purity of from 90% to 100%, preferably from 95% to 100% (according to NMR spectrum).

The compounds I according to the invention can be formulated, for example, as follows:

I. 20 parts by weight of the compound No. 2.08 are dissolved in a mixture which consists of 80 parts by weight of alkylated benzene, 10 parts by weight of the addition product of from 8 to 10 mol of ethylene oxide to 1 mol of oleic acid N-mono-ethanolamide, 5 parts by weight of calcium salt of dodecylbenzenesulfonic acid and 5 parts by weight of the addition product of 40 mol of ethylene oxide to 1 mol of castor oil. By pouring out the solution and finely dispersing it in 100,000 parts by weight of water, an aqueous dispersion is obtained which contains 0.02% by weight of the active compound.

II. 20 parts by weight of the compound No. 2.08 are dissolved in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

III. 20 parts by weight of the active compound No. 2.08 are dissolved in a mixture which consists of 25 parts by weight of cyclohexanone, 65 parts by weight of a mineral oil fraction of boiling point from 210° to 280° C. and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

IV. 20 parts by weight of the active compound No. 2.08 are thoroughly mixed with 3 parts by weight of the sodium salt of diisobutylnaphthalene-α-sulfonic acid, 17 parts by weight of the sodium salt of a lignosulfonic acid from a sulfite waste liquor and 60 parts by weight of powdered silica gel and ground in a hammer mill. By finely dispersing the mixture in 20,000 parts by weight of water, a spray mixture is obtained which contains 0.1% by weight of the active compound.

V. 3 parts by weight of the active compound No. 2.08 are mixed with 97 parts by weight of finely divided kaolin. In this way, a dusting composition is obtained which contains 3% by weight of the active compound.

VI. 20 parts by weight of the active compound No. 2.08 are intimately mixed with 2 parts by weight of calcium salt of dodecylbenzenesulfonic acid, 8 parts by weight of fatty alcohol polyglycol ether, 2 parts by weight of sodium salt of a phenol-urea-formaldehyde condensate and 68 parts by weight of a paraffinic mineral oil. A stable oily dispersion is obtained.

To widen the spectrum of action and to achieve a synergistic effect, the saccharin derivatives can be mixed with numerous representatives of other herbicidal or growth-regulating active compound groups and applied jointly. For example, suitable basic components are diazines, 4 H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1, 3-dione derivatives which carry e.g. a carboxyl or carbimino group in the 2-position, quinolinecarboxylic acid derivatives, imidazolinones, sulfonamides, sulfonylureas, aryloxy- or heteroaryloxyphenoxypropionic acids and their salts, esters and amides and others.

Additionally, it may be useful to apply the compounds I on their own or together in combination with other herbicides, additionally mixed with further crop protection agents, for example with agents for controlling pests or phytopathogenic fungi and bacteria. Further of interest is the miscibility with mineral salt solutions, which are employed for the elimination of nutrition and trace element deficiencies. Non-phytotoxic oils and oil concentrates can also be added.

Depending on the aim of control, time of year, target plants and stage of growth, the application rates of active compound are from 0.001 to 3.0, preferably from 0.01 to 1.0, kg/ha of active substance (a.s.).

PREPARATION EXAMPLES

A) Preparation of the starting substances 1. 2-Methyl-6-acetamidobenzoic acid 90.6 g (0.6 mol) of 6-methylanthranilic acid is added to a solution of 24.8 g (0.62 mol) of NaOH in 500 ml of water and 63.4 g (0.62 mol) of acetic anhydride are then added dropwise. After stirring for one hour, the mixture is acidified to pH 3 with conc. HCl with cooling, and the precipitate which deposits is filtered off with suction, washed with water and dried under reduced pressure at 50° C. Yield: 107 g (0.55 mol) =92% of theory, m.p.: 189°–190° C.

2. 2-Methyl-3-nitro-6-acetamidobenzoic acid 271 ml of 98 percent nitric acid are initially taken at −5° C. and 106 g (0.55 mol) of the 2-methyl-6-acetamidobenzoic acid prepared in 1. are added in portions. After stirring at 10° C. for one hour, the reaction mixture is poured into a mixture of 540 g of ice and 270 ml of water. The deposited precipitate is filtered off with suction, washed with water and dried under reduced pressure at 50° C. Yield: 75.6 g (0.317 mol)=58% of theory, m.p.: 190°–191° C.

The isomer nitrated in the 3-position is deposited from the filtrate after relatively long standing: Yield: 21.3 g (0.089 mol)=16% of theory, m.p.: 180°–182° C.

3. 2-Methyl-3-nitro-6-aminobenzoic acid 450 ml of 2N NaOH are initially taken and 75.6 g (0.317 mol) of 2-methyl-3-nitro-6-acetamidobenzoic acid are added. The reaction mixture is then warmed to 95° C. and is stirred at this temperature for one hour. After cooling to 10° C., it is acidified by addition of 425 ml of 2N HCl, and the precipitate which deposits is filtered off with suction, washed with water and dried under reduced pressure at 50° C. Yield: 50.7 g (0.258 mol)=82% of theory, m.p.: 183°–184° C.

On attempting to remove this acetyl radical in acid, decarboxylation would occur.

4. Methyl 2-methyl-3-nitro-6-aminobenzoate 49.7 g (0.253 mol) of 2-methyl-3-nitro-6-aminobenzoic acid are dissolved in 380 ml of acetone and 43 g (0.51 mol) of sodium hydrogen carbonate are added. The mixture is then heated to boiling until evolution of $CO_2$ is complete. 35.3 g (0.28 mol) of dimethyl sulfate are then added in the course of two hours at the boiling point of acetone to the suspension of the sodium salt of 2-methyl-3-nitro-6-aminobenzoic acid thus obtained, and the mixture is subsequently refluxed for a further 3 hours and then allowed to cool. After pouring the reaction mixture into 1.8 l of water, it is extracted with methylene chloride. After drying, the organic phase is concentrated. The solid obtained is sufficiently pure for the subsequent reaction (NMR). Yield: 50 g (0.238 mol)=94% of theory, m.p.: 92°–94° C.

5. 2-Methoxycarbonyl-3-methyl-4-nitrobenzenesulfonyl chloride 58.5 g (0.278 mol) of methyl 2-methyl-3-nitro-6-aminobenzoate are dissolved with warming in 280 ml of glacial acetic acid and this solution is poured at from 15° to 20° C. into 85 ml of conc. HCl. A solution of 19.3 g (0.28 mol) of sodium nitrite in 60 ml of water is then added dropwise at from 5° to 10° C. and the mixture is stirred at 5° C. for 30 min. This diazonium salt solution is subsequently added dropwise to a solution of 374 g of $SO_2$ in 750 ml of glacial acetic acid which contains 14 g of $CuCl_2$ (dissolved in 30 ml of water). After completion of the evolution of nitrogen, the mixture is stirred for a further 15 min and then poured into 1.4 l of ice-water. The sulfonyl chloride is separated off by extraction with 1.2 l of methylene chloride. After drying and concentrating the organic phase, 73 g (0.25 mol) (=90% of theory) of an oil are obtained, which according to NMR (in $CDCl_3$) is pure 2-methoxycarbonyl-3-methyl-4-nitrobenzenesulfonyl chloride.

6. 4-Methyl-5-nitrosaccharin 104 ml of 25 percent ammonia solution are initially taken, 100 ml of water are added and a solution of 48.7 g (0.166 mol) of 2-methoxycarbonyl-3-methyl-4-nitrobenzenesulfonyl chloride in 70 ml of tetrahydrofuran is then added dropwise at 10° C. After stirring at 25° C. for three hours, water and THF are largely removed and the residue which remains is stirred with ethyl acetate, filtered off with suction and washed with ethyl acetate. After drying under reduced pressure, 34 g (0.131 mol)=79% of theory of a white solid of m.p.: 312° C. (dec.) are obtained.

7. 2,4-Dimethyl-5-nitrosaccharin

This substance can be prepared by subsequent methylation of the saccharin obtained in 6. using dimethyl sulfate in the presence of NaOH.

8. 3-Methyl-4-nitro-2-(N'-methyl)carboxamido-N-methyl-benzenesulfonamide 50 ml of water are poured into 50 ml of 40 percent methylamine solution and a solution of 24.3 g (83 mmol) of 2-methoxycarbonyl-3-methyl-4-nitrobenzenesulfonyl chloride in 35 ml of THF is then added dropwise at 10° C. After stirring for one hour at 25° C., all volatile constituents are removed. The residue is extracted with ethyl acetate, and the organic phase is washed with water, dried and concentrated. The residue which remains crystallizes after relatively long standing. Yield: 10.3 g (40 mmol=48% of theory), m.p.: 125°–126° C., after recrystallization from ethyl acetate m.p.: 144°–145° C.

9. 4-Methyl-5-aminosaccharin 33.6 g (0.13 mol) of 4-methyl-5-nitrosaccharin are dissolved in 1.2 l of water with warming and 5 g of Pd/C (10 percent on active carbon) are added. Hydrogen gas is then passed in with vigorous stirring (pressureless hydrogenation). 9 l of $H_2$ are absorbed in the course of 4.5 hours. After cooling to 25° C., the catalyst is filtered off, and the filtrate is concentrated to a volume of 200 ml and then acidified to pH 1. The deposited precipitate is filtered off with suction, washed with water and dried under reduced pressure at 50° C. 23.4 g (0.11 mol=85% of theory) of a white solid of m.p.: 272°–273° C. are obtained.

10. 4-Methyl-5-iodosaccharin

A mixture of 205 ml of glacial acetic acid, 160 ml of water and 40 ml of conc. HCl is initially taken and 23.4 g (0.11 mol) of 4-methyl-5-aminosaccharin are introduced with stirring at 15°–20° C. 7.9 g (0.115 mol) of sodium nitrite are added dropwise to the resulting suspension at 5°–10° C. and it is stirred at 5° C. for 30 min. The diazonium salt, which is present as a suspension, is then added dropwise in portions to a solution of 19.1 g (0.115 mol) of potassium iodide in 170 ml of water which is warmed to 50° C., nitrogen being formed. After cooling to room temperature, the deposited product is isolated by filtering off with suction, washed with water and dried under reduced pressure at 50° C. 32.5 g (0.1 mol=91% of theory) of a solid of m.p.: 257°–258° C. are obtained. A combustion analysis gave an iodine content of 38.5% (theory 39.3%).

The product is sufficiently pure for the subsequent reactions.

11. 4-Amino-3-methyl-2-(N'-methyl)carboxamido-N-methyl-benzenesulfonamide

In a similar manner to the procedure described in Example 9, the 3-methyl-4-nitro-2-(N'-methyl)carboxamido-N-methylbenzenesulfonamide obtained according to Example 8 is hydrogenated without pressure. The title compound of m.p. 217°–218° C. is obtained in 93% yield.

12. 3-Methyl-4-iodo-2-(N'-methyl)carboxamido-N-methylbenzenesulfonamide

The above compound is diazotized according to the procedure described in Example 10 and converted to the title compound by reaction with KI. Yield: 95% of theory, m.p.: 60°–62° C.

B) Preparation of the intermediates IV 13. 4-Methylsaccharin-5-carboxylic acid 6.4 g (0.002 mol) of 4-methyl-5-iodosaccharin are dissolved in 70 ml of tetramethylurea and 30 ml of water and treated with 0.7 g of bis(triphenylphosphine)palladium chloride and the mixture is heated to 100° C. in a 300 ml autoclave and stirred at a pressure of 100 bar of carbon monoxide for 36 h.

For working up, the mixture is filtered, and water and tetramethylurea are removed by distillation in a high vacuum. The residue is taken up in methyl tert-butyl ether (MTBE), extracted with $NaHCO_3$ soln. and, after acidifying with HCl, extracted again with MTBE. After concentrating, 2.8 g of 4-methylsaccharin-5-carboxylic acid (58% of theory) are obtained.

$^1$H NMR (DMSO, 400.1 MHz): 2.85 (3 H, s); 8.05 (1 H, d); 8.2 (1 H, d);

$^{13}$C NMR (DMSO, 100.6 MHz): 167.4 (CO); 161.3 (CO); 141.6 (quart. C); 139.7 (quart. C); 138.7 (quart. C); 135.6 (CH); 125.4 (quart. C); 118.5 (CH); 15.4 ($CH_3$).

14. 2,4-Dimethylsaccharin-5-carboxylic acid 7.3 g (0.02 mol) of 3-methyl-4-iodo-2-(N'-methyl)carboxamido-N-methylbenzenesulfonamide are initially taken in a 300 ml autoclave, together with 0.69 g of bis(triphenylphosphine)palladium chloride, 30 ml of water and 70 ml of tetramethylurea, and the mixture is heated to 100° C. and stirred at a pressure of 100 bar of carbon monoxide for 36 h.

After working up (as described in Example 13), 4.1 g of the title compound are obtained (0.014 mol=72% of theory).

$^1$H NMR (DMSO, 400.1 MHz): 2.9 (3 H, s); 3.15 (3 H, s); 8.2 (2 H, 2d); 14.0 (1 H, s)

$^{13}$C NMR (DMSO, 100.6 MHz): 167.3 (CO); 158.6 (CO); 139.7 (quart. C); 139.1 (quart. C); 138.9 (quart. C); 135.5 (CH); 124.6 (quart. C); 119.0 (CH); 22.9 ($CH_3$); 15.6 ($CH_3$).

15. 2,4-Dimethylsaccharin-5-carbonyl chloride 3.8 g (14.9 mmol) of 2,4-dimethylsaccharin-5-carboxylic acid are suspended in 100 ml of toluene, and the mixture is heated to 80° C. and 3.5 g (29.8 mmol) of thionyl chloride are added dropwise. After refluxing for two hours, the solution is decanted hot and the reaction mixture is concentrated. Yield: 74% of theory, m.p.: 149°–150° C.

The saccharincarbonyl chloride V compiled in Table 8 can be obtained in a similar manner.

C) Conversion of the intermediates V to the herbicidally active final products I.

16. Acylation of cyclohexanedione

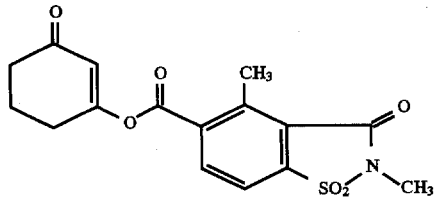

1.21 g (12 mmol) of triethylamine are poured into a suspension of 1.23 g (10.9 mmol) of cyclohexane-1,3-dione in 50 ml of methylene chloride and a solution of 3 g (10.9 mmol) of 2,4- dimethylsaccharin-5-carbonyl chloride in 60 ml of methylene chloride is then added dropwise at 25° C. The mixture is then stirred at 40° C. for 7 hours. After cooling, 60 ml of water are poured in, and the methylene chloride phase is separated off in a separating funnel and dried over magnesium sulfate. The amorphous residue (2.5 g) which remains after stripping off the solvent is the enol ester, which is rearranged in the next stage without further purification.

17. Rearrangement to the final product I

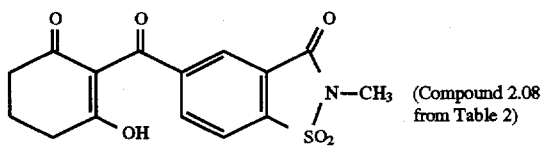

(Compound 2.08 from Table 2)

2.5 g (7.2 mmol) of the above enol ester are dissolved in 80 ml of acetonitrile, treated with 3.5 ml of triethylamine and then with 0.33 g (4 mmol) of acetone cyanohydrin and stirred for 16 h. 24.5 g of 5 percent HCl are then added and the reaction mixture is extracted with 100 ml of methylene chloride. The organic phase is then extracted with 5 percent potassium carbonate solution, the product passing into the aqueous phase. By acidifying the alkaline-aqueous soloution with conc. HCl, a gum-like solid is precipitated which crystallizes after triturating with diisopropyl ether. After washing with petroleum ether, it is dried under reduced pressure. Yield: 0.88 g (35% of theory)

The compounds below are obtained in a similar manner:

The groups mentioned in Tables 1 to 8 for a substituent are additionally considered per se as a particularly preferred definition of the substituents concerned, independently of the special combination with other substituents under which they are mentioned.

TABLE 1

Saccharin-4-yl-substituted cyclohexane-1,3-diones

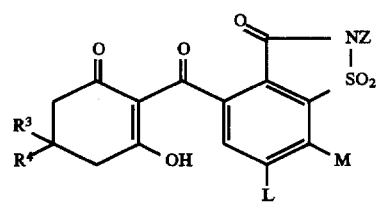

| No. | $R^3$ | $R^4$ | L | M | Z | M.p. °C. |
|---|---|---|---|---|---|---|
| 1.01 | H | H | H | H | H | 202–204 |
| 1.02 | H | H | H | H | $CH_3$ | |
| 1.03 | H | H | H | H | $C_2H_5$ | |
| 1.04 | H | H | H | H | Allyl | |
| 1.05 | H | H | H | H | Propargyl | |
| 1.06 | H | H | H | H | Phenyl | |
| 1.07 | H | H | $CH_3$ | H | H | |
| 1.08 | H | H | $CH_3$ | H | $CH_3$ | |
| 1.09 | H | H | $CH_3$ | H | $C_2H_5$ | |
| 1.10 | H | H | $CH_3$ | H | Allyl | |
| 1.11 | H | H | $CH_3$ | H | Propargyl | |
| 1.12 | H | H | $CH_3$ | H | Phenyl | |
| 1.13 | H | H | Cl | H | H | |
| 1.14 | H | H | Cl | H | $CH_3$ | |
| 1.15 | H | H | Cl | H | $C_2H_5$ | |
| 1.16 | H | H | Cl | H | Allyl | |

TABLE 1-continued

Saccharin-4-yl-substituted cyclohexane-1,3-diones

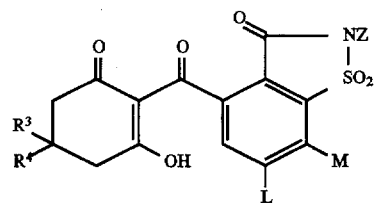

| No. | $R^3$ | $R^4$ | L | M | Z | M.p. °C. |
|---|---|---|---|---|---|---|
| 1.17 | H | H | Cl | H | Propargyl | |
| 1.18 | H | H | Cl | H | Phenyl | |
| 1.19 | H | H | H | $CH_3$ | H | |
| 1.20 | H | H | H | $CH_3$ | $CH_3$ | |
| 1.21 | H | H | H | $CH_3$ | $C_2H_5$ | |
| 1.22 | W | H | H | $CH_3$ | Allyl | |
| 1.23 | H | H | H | $CH_3$ | Propargyl | |
| 1.24 | H | H | H | $CH_3$ | Phenyl | |
| 1.25 | H | H | H | Cl | H | |
| 1.26 | H | H | H | Cl | $CH_3$ | |
| 1.27 | H | H | H | Cl | $C_2H_5$ | |
| 1.28 | H | H | H | Cl | Allyl | |
| 1.29 | H | H | H | Cl | Propargyl | |
| 1.30 | H | H | H | Cl | Phenyl | |
| 1.31 | H | H | H | $OCH_3$ | H | |
| 1.32 | H | H | H | $OCH_3$ | $CH_3$ | |
| 1.33 | H | H | H | $OCH_3$ | $C_2H_5$ | |
| 1.34 | H | H | H | $OCH_3$ | Allyl | |
| 1.35 | H | H | H | $OCH_3$ | Propargyl | |
| 1.36 | H | H | H | $OCH_3$ | Phenyl | |
| 1.37 | H | H | $OCH_3$ | H | H | |
| 1.38 | H | H | $OCH_3$ | H | $CH_3$ | |
| 1.39 | H | H | $OCH_3$ | H | $C_2H_5$ | |
| 1.40 | H | H | $OCH_3$ | H | Allyl | |
| 1.41 | H | H | $OCH_3$ | H | Propargyl | |
| 1.42 | H | H | $OCH_3$ | H | Phenyl | |
| 1.43 | H | H | H | $NO_2$ | H | |
| 1.44 | H | H | H | $NO_2$ | $CH_3$ | |
| 1.45 | H | H | H | $NO_2$ | $C_2H_5$ | |
| 1.46 | H | H | H | $NO_2$ | Allyl | |
| 1.47 | H | H | H | $NO_2$ | Propargyl | |
| 1.48 | H | H | H | $NO_2$ | Phenyl | |
| 1.49 | H | H | CN | H | H | |
| 1.50 | H | H | CN | H | $CH_3$ | |
| 1.51 | H | H | CN | H | $C_2H_5$ | |
| 1.52 | H | H | CN | H | Allyl | |
| 1.53 | H | H | CN | H | Propargyl | |
| 1.54 | H | H | CN | H | Phenyl | |
| 1.55 | H | H | $CF_3$ | H | H | |
| 1.56 | H | H | $CF_3$ | H | $CH_3$ | |
| 1.57 | H | H | $CF_3$ | H | $C_2H_5$ | |
| 1.58 | H | H | $CF_3$ | H | Allyl | |
| 1.59 | H | H | $CF_3$ | H | Propargyl | |
| 1.60 | H | H | $CF_3$ | H | Phenyl | |
| 1.61 | $CH_3$ | $CH_3$ | H | H | H | 224–225 |
| 1.62 | $CH_3$ | $CH_3$ | H | H | $CH_3$ | 177–180 |

TABLE 2

Saccharin-5-yl-substituted cyclohexane-1,3-diones

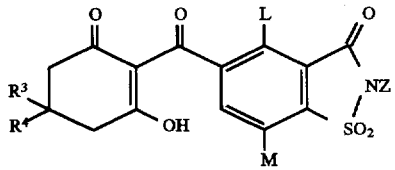

| No. | R³ | R⁴ | L | M | Z | M.p.°C. |
|---|---|---|---|---|---|---|
| 2.01 | H | H | H | H | H | |
| 2.02 | H | H | H | H | H | |
| 2.03 | H | H | H | H | C₂H₅ | |
| 2.04 | H | H | H | H | Allyl | |
| 2.05 | H | H | H | H | Propargyl | |
| 2.06 | H | H | H | H | Phenyl | |
| 2.07 | H | H | CH₃ | H | H | 280–282 |
| 2.08 | H | H | CH₃ | H | CH₃ | 180 |
| 2.09 | H | H | CH₃ | H | C₂H₅ | |
| 2.10 | H | H | CH₃ | H | Allyl | |
| 2.11 | H | H | CH₃ | H | Propargyl | |
| 2.12 | H | H | CH₃ | H | Phenyl | |
| 2.13 | H | H | Cl | H | H | |
| 2.14 | H | H | Cl | H | CH₃ | |
| 2.15 | H | H | Cl | H | C₂H₅ | |
| 2.16 | H | H | Cl | H | Allyl | |
| 2.17 | H | H | Cl | H | Propargyl | |
| 2.18 | H | H | Cl | H | Phenyl | |
| 2.19 | H | H | H | CH₃ | H | |
| 2.20 | H | H | H | CH₃ | CH₃ | |
| 2.21 | H | H | H | CH₃ | C₂H₅ | |
| 2.22 | H | H | H | CH₃ | Allyl | |
| 2.23 | H | H | H | CH₃ | Propargyl | |
| 2.24 | H | H | H | CH₃ | Phenyl | |
| 2.25 | H | H | H | H | H | |
| 2.26 | H | H | H | H | CH₃ | |
| 2.27 | H | H | H | H | C₂H₅ | |
| 2.28 | H | H | H | H | Allyl | |
| 2.29 | H | H | H | H | Propargyl | |
| 2.30 | H | H | H | H | Phenyl | |
| 2.31 | H | H | H | OCH₃ | H | |
| 2.32 | H | H | H | OCH₃ | CH₃ | |
| 2.33 | H | H | H | OCH₃ | C₂H₅ | |
| 2.34 | H | H | H | OCH₃ | Allyl | |
| 2.35 | H | H | H | OCH₃ | Propargyl | |
| 2.36 | H | H | H | OCH₃ | Phenyl | |
| 2.37 | H | H | OCH₃ | H | H | |
| 2.38 | H | H | OCH₃ | H | CH₃ | |
| 2.39 | H | H | OCH₃ | H | C₂H₅ | |
| 2.40 | H | H | OCH₃ | H | Allyl | |
| 2.41 | H | H | OCH₃ | H | Propargyl | |
| 2.42 | H | H | OCH₃ | H | Phenyl | |
| 2.43 | H | H | NO₂ | H | H | |
| 2.44 | H | H | NO₂ | H | CH₃ | |
| 2.45 | H | H | NO₂ | H | C₂H₅ | |
| 2.46 | H | H | NO₂ | H | Allyl | |
| 2.47 | H | H | NO₂ | H | Propargyl | |
| 2.48 | H | H | NO₂ | H | Phenyl | |
| 2.49 | H | H | CN | H | H | |
| 2.50 | H | H | CN | H | CH₃ | |
| 2.51 | H | H | CN | H | C₂H₅ | |
| 2.52 | H | H | CN | H | Allyl | |
| 2.53 | H | H | CN | H | Propargyl | |
| 2.54 | H | H | CN | H | Phenyl | |
| 2.55 | H | H | CF₃ | H | H | |
| 2.56 | H | H | CF₃ | H | CH₃ | |
| 2.57 | H | H | CF₃ | H | C₂H₅ | |
| 2.58 | H | H | CF₃ | H | Allyl | |
| 2.59 | H | H | CF₃ | H | Propargyl | |
| 2.60 | H | H | CF₃ | H | Phenyl | |
| 2.61 | H | CH₃ | CH₃ | H | CH₃ | |
| 2.62 | CH₃ | CH₃ | CH₃ | H | CH₃ | |
| 2.63 | H | H | CH₃ | CH₃ | CH₃ | |
| 2.64 | CH₃ | H | CH₃ | CH₃ | CH₃ | |
| 2.65 | H | CH₃ | CH₃ | CH₃ | C₂H₅ | |

TABLE 2-continued

Saccharin-5-yl-substituted cyclohexane-1,3-diones

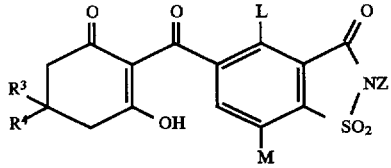

| No. | R³ | R⁴ | L | M | Z | M.p.°C. |
|---|---|---|---|---|---|---|
| 2.66 | H | H | OCH₃ | CH₃ | CH₃ | |
| 2.67 | CH₃ | H | OCH₃ | CH₃ | CH₃ | |
| 2.68 | CH₃ | CH₃ | OCH₃ | CH₃ | CH₃ | |
| 2.69 | H | CH₃ | OCH₃ | CH₃ | C₂H₅ | |
| 2.70 | H | H | OCH₃ | Cl | CH₃ | |
| 2.71 | CH₃ | H | OCH₃ | Cl | CH₃ | |
| 2.72 | CH₃ | CH₃ | OCH₃ | Cl | CH₃ | |

TABLE 3

Saccharin-5-yl-substituted cyHohexane-1,3-diones

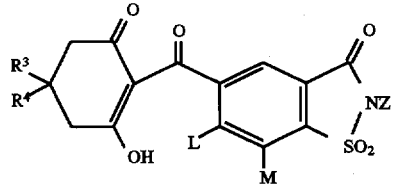

| No. | R³ | R⁴ | L | M | Z | M.p.°C. |
|---|---|---|---|---|---|---|
| 3.01 | H | H | CH₃ | H | H | |
| 3.02 | H | H | CH₃ | H | CH₃ | |
| 3.03 | H | H | CH₃ | H | C₂H₅ | |
| 3.04 | H | H | CH₃ | H | Allyl | |
| 3.05 | H | H | CH₃ | H | Propargyl | |
| 3.06 | H | H | CH₃ | H | Phenyl | |
| 3.07 | H | H | CH₃ | CH₃ | H | |
| 3.08 | H | H | CH₃ | CH₃ | CH₃ | |
| 3.09 | H | H | CH₃ | CH₃ | C₂H₅ | |
| 3.10 | H | H | CH₃ | CH₃ | Allyl | |
| 3.11 | H | H | CH₃ | CH₃ | Propargyl | |
| 3.12 | H | H | CH₃ | CH₃ | Phenyl | |
| 3.13 | H | H | H | H | H | |
| 3.14 | H | H | H | H | CH₃ | |
| 3.15 | H | H | H | H | C₂H₅ | |
| 3.16 | H | H | H | H | Allyl | |
| 3.17 | H | H | H | H | Propargyl | |
| 3.18 | H | H | H | H | Phenyl | |
| 3.19 | H | H | CH₃ | Cl | H | |
| 3.20 | H | H | CH₃ | Cl | CH₃ | |
| 3.21 | H | H | CH₃ | Cl | C₂H₅ | |
| 3.22 | H | H | CH₃ | Cl | Allyl | |
| 3.23 | H | H | CH₃ | Cl | Propargyl | |
| 3.24 | H | H | CH₃ | Cl | Phenyl | |
| 3.25 | H | H | OCH₃ | H | H | |
| 3.26 | H | H | OCH₃ | H | CH₃ | |
| 3.27 | H | H | OCH₃ | H | C₂H₅ | |
| 3.28 | H | H | OCH₃ | H | Allyl | |
| 3.29 | H | H | OCH₃ | H | Propargyl | |
| 3.30 | H | H | OCH₃ | H | Phenyl | |
| 3.31 | H | H | CH₃ | OCH₃ | H | |
| 3.32 | H | H | CH₃ | OCH₃ | CH₃ | |
| 3.33 | H | H | CH₃ | OCH₃ | C₂H₅ | |
| 3.34 | H | H | CH₃ | OCH₃ | Allyl | |
| 3.35 | H | H | CH₃ | OCH₃ | Propargyl | |
| 3.36 | H | H | CH₃ | OCH₃ | Phenyl | |
| 3.37 | H | H | OCH₃ | H | H | |
| 3.38 | H | H | OCH₃ | H | CH₃ | |

TABLE 3-continued

Saccharin-5-yl-substituted cyHohexane-1,3-diones

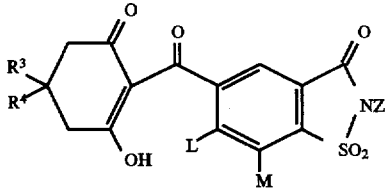

| No. | R³ | R⁴ | L | M | Z | M.p.°C. |
|---|---|---|---|---|---|---|
| 3.39 | H | H | OCH₃ | H | C₂H₅ | |
| 3.40 | H | H | OCH₃ | H | Allyl | |
| 3.41 | H | H | OCH₃ | H | Propargyl | |
| 3.42 | H | H | OCH₃ | H | Phenyl | |
| 3.43 | H | H | NO₂ | H | H | |
| 3.44 | H | H | NO₂ | H | CH₃ | |
| 3.45 | H | H | NO₂ | H | C₂H₅ | |
| 3.46 | H | H | NO₂ | H | Allyl | |
| 3.47 | H | H | NO₂ | H | Propargyl | |
| 3.48 | H | H | NO₂ | H | Phenyl | |
| 3.49 | H | H | SO₂CH₃ | H | H | |
| 3.50 | H | H | SO₂CH₃ | H | CH₃ | |
| 3.51 | H | H | SO₂CH₃ | H | C₂H₅ | |
| 3.52 | H | H | SO₂CH₃ | H | Allyl | |
| 3.53 | H | H | SO₂CH₃ | H | Propargyl | |
| 3.54 | H | H | SO₂CH₃ | H | Phenyl | |
| 3.55 | H | H | CF₃ | H | H | |
| 3.56 | H | H | CF₃ | H | CH₃ | |
| 3.57 | H | H | CF₃ | H | C₂H₅ | |
| 3.58 | H | H | CF₃ | H | Allyl | |
| 3.59 | H | H | CF₃ | H | Propargyl | |
| 3.60 | H | H | CF₃ | H | Phenyl | |
| 3.61 | CH₃ | CH₃ | CH₃ | H | CH₃ | 178–180 |
| 3.62 | CH₃ | H | CH₃ | H | CH₃ | |

TABLE 4

Saccharin-6-yl-substituted cyHohexane-1,3-diones

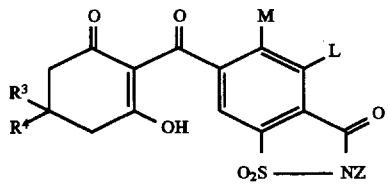

| No. | R³ | R⁴ | L | M | Z | M.p.°C. |
|---|---|---|---|---|---|---|
| 4.01 | H | H | H | H | H | |
| 4.02 | H | H | H | H | CH₃ | |
| 4.03 | H | H | H | H | C₂H₅ | |
| 4.04 | H | H | H | H | Allyl | |
| 4.05 | H | H | H | H | Propargyl | |
| 4.06 | H | H | H | H | Phenyl | |
| 4.07 | H | H | CH₃ | H | H | |
| 4.08 | H | H | CH₃ | H | CH₃ | |
| 4.09 | H | H | CH₃ | H | C₂H₅ | |
| 4.10 | H | H | CH₃ | H | Allyl | |
| 4.11 | H | H | CH₃ | H | Propargyl | |
| 4.12 | H | H | CH₃ | H | Phenyl | |
| 4.13 | H | H | Cl | H | H | |
| 4.14 | H | H | Cl | H | CH₃ | |
| 4.15 | H | H | Cl | H | C₂H₅ | |
| 4.16 | H | H | Cl | H | Allyl | |
| 4.17 | H | H | Cl | H | Propargyl | |
| 4.18 | H | H | Cl | H | Phenyl | |
| 4.19 | H | H | H | CH₃ | H | |
| 4.20 | H | H | H | CH₃ | H | |

TABLE 4-continued

Saccharin-6-yl-substituted cyHohexane-1,3-diones

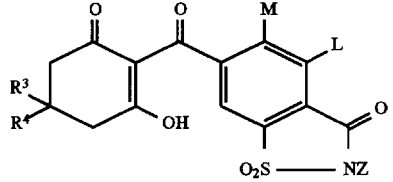

| No. | R³ | R⁴ | L | M | Z | M.p.°C. |
|---|---|---|---|---|---|---|
| 4.21 | H | H | H | CH₃ | C₂H₅ | |
| 4.22 | H | H | H | CH₃ | Allyl | |
| 4.23 | H | H | H | CH₃ | Propargyl | |
| 4.24 | H | H | H | CH₃ | Phenyl | |
| 4.25 | H | H | H | H | H | |
| 4.26 | H | H | H | H | CH₃ | |
| 4.27 | H | H | H | H | C₂H₅ | |
| 4.28 | H | H | H | H | Allyl | |
| 4.29 | H | H | H | H | Propargyl | |
| 4.30 | H | H | H | H | Phenyl | |
| 4.31 | H | H | H | OCH₃ | H | |
| 4.32 | H | H | H | OCH₃ | CH₃ | |
| 4.33 | H | H | H | OCH₃ | C₂H₅ | |
| 4.34 | H | H | H | OCH₃ | Allyl | |
| 4.35 | H | H | H | OCH₃ | Propargyl | |
| 4.36 | H | H | H | OCH₃ | Phenyl | |
| 4.37 | H | H | OCH₃ | H | H | |
| 4.38 | H | H | OCH₃ | H | CH₃ | |
| 4.39 | H | H | OCH₃ | H | C₂H₅ | |
| 4.40 | H | H | OCH₃ | H | Allyl | |
| 4.41 | H | H | OCH₃ | H | Propargyl | |
| 4.42 | H | H | OCH₃ | H | Phenyl | |
| 4.43 | H | H | H | NO₂ | H | |
| 4.44 | H | H | H | NO₂ | CH₃ | |
| 4.45 | H | H | H | NO₂ | C₂H₅ | |
| 4.46 | H | H | H | NO₂ | Allyl | |
| 4.47 | H | H | H | NO₂ | Propargyl | |
| 4.48 | H | H | H | NO₂ | Phenyl | |
| 4.49 | H | H | H | CN | H | |
| 4.50 | H | H | H | CN | CH₃ | |
| 4.51 | H | H | H | CN | C₂H₅ | |
| 4.52 | H | H | H | CN | Allyl | |
| 4.53 | H | H | H | CN | Propargyl | |
| 4.54 | H | H | H | CN | Phenyl | |
| 4.55 | H | H | H | CF₃ | H | |
| 4.56 | H | H | H | CF₃ | CH₃ | |
| 4.57 | H | H | H | CF₃ | C₂H₅ | |
| 4.58 | H | H | H | CF₃ | Allyl | |
| 4.59 | H | H | H | CF₃ | Propargyl | |
| 4.60 | H | H | H | CF₃ | Phenyl | |
| 4.61 | CH₃ | H | CH₃ | H | H | 184–186 |
| 4.62 | CH₃ | H | CH₃ | H | CH₃ | 180–181 |
| 4.63 | CH₃ | H | CH₃ | H | Phenyl | 325–330 |
| 4.64 | H | H | CH₃ | H | CH₃ | >200 |

TABLE 5

Saccharin-6-yl-substituted CyHohexane-1,3-diones

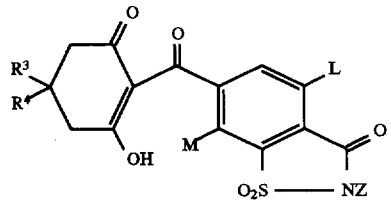

| No. | R³ | R⁴ | L | M | Z | M.p.°C. |
|---|---|---|---|---|---|---|
| 5.01 | H | H | CH₃ | CH₃ | H | |
| 5.02 | H | H | CH₃ | CH₃ | CH₃ | |
| 5.03 | H | H | CH₃ | CH₃ | C₂H₅ | |
| 5.04 | H | H | CH₃ | CH₃ | Allyl | |
| 5.05 | H | H | CH₃ | CH₃ | Propargyl | |
| 5.06 | H | H | CH₃ | CH₃ | Phenyl | |
| 5.07 | H | H | CH₃ | OCH₃ | H | |
| 5.08 | H | H | CH₃ | OCH₃ | H | |
| 5.09 | W | H | CH₃ | OCH₃ | C₂H₅ | |
| 5.10 | H | H | CH₃ | OCH₃ | Allyl | |
| 5.11 | H | H | CH₃ | OCH₃ | Propargyl | |
| 5.12 | H | H | CH₃ | OCH₃ | Phenyl | |
| 5.13 | H | H | Cl | Cl | H | |
| 5.14 | H | H | Cl | Cl | CH₃ | |
| 5.15 | H | H | Cl | Cl | C₂H₅ | |
| 5.16 | H | H | Cl | Cl | Allyl | |
| 5.17 | H | H | Cl | Cl | Propargyl | |
| 5.18 | H | H | Cl | Cl | Phenyl | |
| 5.19 | H | H | Cl | CH₃ | H | |
| 5.20 | H | H | Cl | CH₃ | H | |
| 5.21 | H | H | Cl | CH₃ | C₂H₅ | |
| 5.22 | H | H | Cl | CH₃ | Allyl | |
| 5.23 | H | H | Cl | CH₃ | Propargyl | |
| 5.24 | H | H | Cl | CH₃ | Phenyl | |
| 5.25 | H | H | CH₃ | H | H | |
| 5.26 | H | H | CH₃ | H | CH₃ | |
| 5.27 | H | H | CH₃ | H | C₂H₅ | |
| 5.28 | H | H | CH₃ | H | Allyl | |
| 5.29 | H | H | CH₃ | H | Propargyl | |
| 5.30 | H | H | CH₃ | H | Phenyl | |
| 5.31 | H | H | CH₃ | SCH₃ | H | |
| 5.32 | H | H | CH₃ | SCH₃ | CH₃ | |
| 5.33 | H | H | CH₃ | SCH₃ | C₂H₅ | |
| 5.34 | H | H | CH₃ | SCH₃ | Allyl | |
| 5.35 | H | H | CH₃ | SCH₃ | Propargyl | |
| 5.36 | H | H | CH₃ | SCH₃ | Phenyl | |
| 5.37 | H | H | OCH₃ | CH₃ | H | |
| 5.38 | H | H | OCH₃ | CH₃ | CH₃ | |
| 5.39 | H | H | OCH₃ | CH₃ | C₂H₅ | |
| 5.40 | H | H | OCH₃ | CH₃ | Allyl | |
| 5.41 | H | H | OCH₃ | CH₃ | Propargyl | |
| 5.42 | H | H | OCH₃ | CH₃ | Phenyl | |
| 5.43 | H | H | H | OCH₃ | H | |
| 5.44 | H | H | H | OCH₃ | CH₃ | |
| 5.45 | H | H | H | OCH₃ | C₂H₅ | |
| 5.46 | H | H | H | OCH₃ | Allyl | |
| 5.47 | H | H | H | OCH₃ | Propargyl | |
| 5.48 | H | H | H | OCH₃ | Phenyl | |
| 5.49 | H | H | CN | Cl | H | |
| 5.50 | H | H | CN | Cl | CH₃ | |
| 5.51 | H | H | CN | Cl | C₂H₅ | |
| 5.52 | H | H | CN | Cl | Allyl | |
| 5.53 | H | H | CN | Cl | Propargyl | |
| 5.54 | H | H | CN | Cl | Phenyl | |
| 5.55 | H | H | CF₃ | CH₃ | H | |
| 5.56 | H | H | CF₃ | CH₃ | CH₃ | |
| 5.57 | H | H | CF₃ | CH₃ | C₂H₅ | |
| 5.58 | H | H | CF₃ | CH₃ | Allyl | |
| 5.59 | H | H | CF₃ | CH₃ | Propargyl | |
| 5.60 | H | H | CF₃ | CH₃ | Phenyl | |

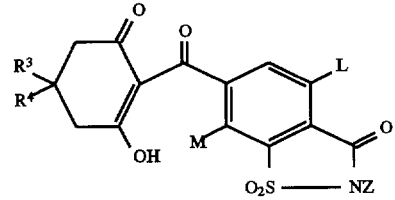

TABLE 6

CyHohexane-1,3-diones substituted in the cyHohexane ring, of the type

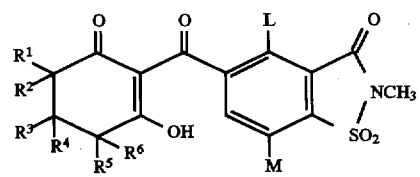

| No. | R¹, R² | R⁵, R⁶ | R³ | R⁴ | L | M | M.p.°C. |
|---|---|---|---|---|---|---|---|
| 6.01 | H | H | H | 2-Ethylthiopropyl | CH₃ | H | |
| 6.02 | H | H | H | Tetrahydropyran-3-yl | CH₃ | H | |
| 6.03 | H | H | H | Tetrahydropyran-4-yl | CH₃ | H | |
| 6.04 | H | H | H | Tetrahydro-thiopyran-3-yl | CH₃ | H | |
| 6.05 | H | H | H | 1-Methylthio-cyHopropyl | CH₃ | H | |

TABLE 7

Saccharin-5-yl-substituted bicyclo[4.1.0]heptanediones

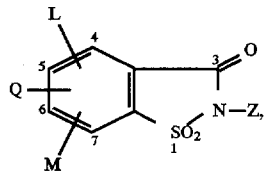

| No. | L | M | Z | M.p.°C. |
|---|---|---|---|---|
| 7.01 | H | H | H | |
| 7.02 | H | H | CH₃ | |
| 7.03 | CH₃ | H | H | |
| 7.04 | CH₃ | H | CH₃ | |
| 7.05 | CH₃ | H | 2-Chlorophenyl | |
| 7.06 | CH₃ | H | 3-Chlorophenyl | |
| 7.07 | CH₃ | H | 4-Chlorophenyl | |
| 7.08 | CH₃ | H | 4-Chlorobenzyl | |
| 7.09 | CH₃ | H | 4-Methylbenzyl | |
| 7.10 | CH₃ | CH₃ | CH₃ | |
| 7.11 | CH₃ | H | C₂H₅ | |
| 7.12 | H | H | Propargyl | |

Use examples

It was possible to show the herbicidal action of the saccharin derivatives of the formula I by greenhouse tests:

The cultivation vessels used were plastic flower pots containing loamy sand with about 3.0% humus as a substrate. The seeds of the test plants were sown separately according to species.

In the case of preemergence treatment, the active compounds suspended or emulsified in water were applied directly after sowing by means of finely dispersing nozzles. The vessels were lightly water in order to promote germination and growth, and then covered with transparent plastic hoods until the plants had taken root. This covering causes a uniform germination of the test plants if this is not adversely affected by the active compounds.

For the purpose of postemergence treatment, the test plants were first raised, according to growth form, to a height of growth of from 3 to 15 cm and only then treated with the active compounds suspended or emulsified in water. For this purpose, the test plants were either sown directly and raised in the same vessels or they were first raised separately as seed plants and transplanted into the test vessels a few days before the treatment. The application rates for postemergence treatment was 0.5 or 0.25 kg/ha of a.s.

The plants were kept species-specifically at from 10° to 25° C. or 20° to 35° C. The test period extended over 2 to 4 weeks. During this time, the plants were tended and their reaction to the individual treatments was assessed.

Rating was carried out on a scale of from 0 to 100. 100 in this case means no emergence of the plants or complete destruction of at least the above-ground parts and 0 means no damage or normal course of growth.

The plants used in the greenhouse tests were made up of the following species:

| Botanical name | Common name |
|---|---|
| *Alopecurus myosuroides* | blackgrass |
| *Avena fatua* | wild oats |
| *Zea mays* | Indian corn |

At an application rate of 0.5 or 0.25 kg/ha of a.s., undesiredplants can be very effectively controlled postemergence using the compound from Example 2.08.

We claim:

1. A saccharin derivative of the formula I $$\text{I}$$

where the substituents have the following meanings:

L and M are hydrogen, $C_1$-$C_4$-alkyl, $C_1$-$C_4$-alkoxy, $C_1$-$C_4$-alkylthio, chlorine, cyano, methylsulfonyl, nitro or trifluoromethyl;

Z is hydrogen, $C_1$-$C_4$-alkyl, $C_3$-$C_8$-cycloalkyl, $C_3$-$C_6$-alkenyl, $C_3$-$C_5$-alkynyl, $C_1$-$C_4$-acyl, benzyl or phenyl, the phenyl rings in each case being unsubstituted or substituted by halogen or $C_1$-$C_4$-alkyl;

Q is a radical CO—J;

J is a 2-linked cyclohexane-1,3-dione ring of the formula II

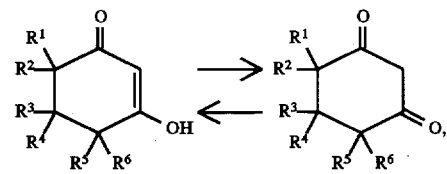

where either $R^1$ to $R^6$ are hydrogen or methyl, or, if $R^1$, $R^2$, $R^3$, $R^5$ and $R^6$ are hydrogen, $R^4$ is 2-ethylthiopropyl, tetrahydropyran-3-yl, tetrahydropyran-4-yl, tetrahydrothiopyran-3-yl or 1-methylthiocyclopropyl, or, if $R^1$, $R^4$ and $R^5$ are hydrogen and $R^6$ is methyl, $R^2$ and $R^3$ form a three-membered ring such that a 2-linked bicyclo[4.1.0]heptane ring of the formula III results

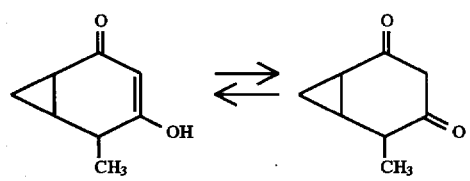

and agriculturally customary salts of the compounds I.

2. A saccharin derivative of the formula I as claimed in claim 1, where L is $C_1$-$C_4$-alkyl, $C_1$-$C_4$-alkoxy, $C_1$-$C_4$-alkylthio, chlorine, cyano, methylsulfonyl, nitro or trifluoromethyl and M is hydrogen or $C_1$-$C_4$-alkyl, $C_1$-$C_4$-alkoxy, $C_1$-$C_4$-alkylthio, chlorine, cyano, methylsulfonyl, nitro or trifluoromethyl.

3. A saccharin derivative of the formula I as claimed in claim 1, where the radicals L and M are hydrogen, methyl, methoxy, methylthio, chlorine, cyano, methylsulfonyl, nitro or trifluoromethyl.

4. A herbicidal composition containing at least one saccharin derivative of the formula I as claimed in claim 1 and customary inert additives.

5. A method of controlling undesired plant growth, which comprises allowing a herbicidally active amount of a saccharin derivative of the formula I as claimed in claim 1 to act on the plants or their habitat.

6. A process for preparing the compounds of the formula I as claimed in claim 1, which comprises acylating the respective starting substances of the formulae II or III

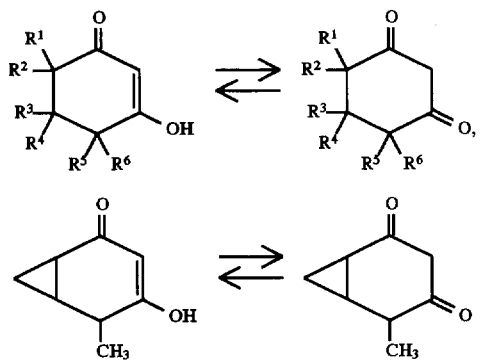

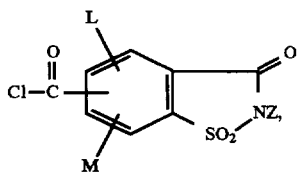

with an acid chloride of the formula V

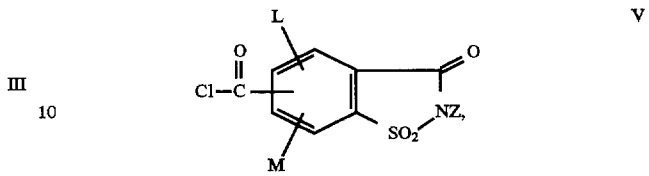

where L, M and Z have the meanings mentioned in claim 1, and rearranging the acylation product to the compounds I in the presence of a catalyst.

7. A saccharin derivative of the formula V

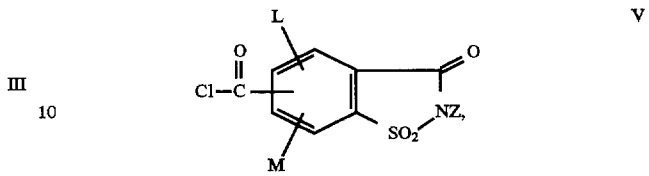

where L, M and Z have the following meanings:

L and M are hydrogen, $C_1$–$C_4$-alkyl, $C_1$–$C_4$-alkoxy, $C_1$–$C_4$-alkylthio, chlorine, cyano, methylsulfonyl, nitro or trifluoromethyl;

Z is hydrogen, $C_1$–$C_4$-alkyl, $C_3$–$C_8$-cycloalkyl, $C_3$–$C_6$-alkenyl, $C_3$–$C_5$-alkynyl, $C_1$–$C_4$-acyl, benzyl or phenyl, in each case unsubstituted or substituted by halogen or $C_1$–$C_4$-alkyl in the phenyl ring.

* * * * *